US00PP35517P2

(12) United States Plant Patent
Chaussard

(10) Patent No.: US PP35,517 P2
(45) Date of Patent: Dec. 5, 2023

(54) ***ABELIA* PLANT NAMED 'MINABAUT01'**

(50) Latin Name: *Abelia chinensis*
Varietal Denomination: Minabaut01

(71) Applicant: HORTIVAL DIFFUSION, Beaufort en Anjou (FR)

(72) Inventor: Pierre Chaussard, Saint Mathurin sur Loire (FR)

(73) Assignee: HORTIVAL DIFFUSION, Beaufort en Anjou (FR)

( * ) Notice: Subject to any disclaimer, the term of this patent is extended or adjusted under 35 U.S.C. 154(b) by 0 days.

(21) Appl. No.: 18/093,322

(22) Filed: Jan. 4, 2023

(51) Int. Cl.
*A01H 6/00* (2018.01)
*A01H 5/00* (2018.01)

(52) U.S. Cl.
USPC ..... Plt./226

(58) Field of Classification Search
USPC ..... Plt./226
See application file for complete search history.

(56) References Cited

U.S. PATENT DOCUMENTS

PP21,632 P2 * 1/2011 Keiser ..... A01H 6/00
Plt./226

* cited by examiner

*Primary Examiner* — Karen M Redden
(74) *Attorney, Agent, or Firm* — Penny J. Aguirre

(57) ABSTRACT

A new cultivar of *Abelia chinensis* plant named 'Minabaut01' that is characterized by its upright and well branched plant habit, its flowers with petals that are lavender on the outer surface and white on the inner surface in color and sepals that are pink in color, its floriferous blooming habit, its flowers that show coloration early in the season, its leaves that are deep green in color, and its flowers with a moderate fragrance.

2 Drawing Sheets

Botanical classification: *Abelia chinensis.*
Varietal denomination: 'Minabaut01'.

CROSS REFERENCE TO A RELATED APPLICATION

This application is related to a European plant breeders' rights application filed on Oct. 29, 2021, application No. 2021/2718.

BACKGROUND OF THE INVENTION

The present invention relates to a new and distinct cultivar of *Abelia chinensis* and will be referred to hereafter by its cultivar name, 'Minabaut01'. 'Minabaut01' represents a new *Abelia*, a semi-evergreen shrub grown for landscape use.

'Minabaut01' originated as a chance seedling in September of 2014 that was growing in a field planted with unnamed and unpatented plants of *Abelia chinensis* from the Inventor's breeding program in La Menitre, France. The exact parents are therefore unknown.

Asexual propagation of the new cultivar was first accomplished by stem cuttings in September 2014 by the Inventor in La Menitre, France. Asexual propagation by stem cuttings has determined the characteristics of the new cultivar are stable and reproduced true to type in successive generations.

SUMMARY OF THE INVENTION

The following traits have been repeatedly observed and represent the characteristics of the new cultivar. These attributes in combination distinguish 'Minabaut01' as a unique cultivar of *Abelia.*

1. 'Minabaut01' exhibits an upright and well branched plant habit.
2. 'Minabaut01' exhibits flowers with petals that are white in color and sepals that are pink in color.
3. 'Minabaut01' exhibits a floriferous blooming habit.
4. 'Minabaut01' exhibits flowers that show coloration early in the season.
5. 'Minabaut01' exhibits leaves that are deep green in color.
6. 'Minabaut01' exhibits flowers with a moderate fragrance.

Typical plants of *Abelia chinensis* that were in the growing area in which 'Minabaut01' was discovered are similar to 'Minabaut01' in flower form and flower size but differ from 'Minabaut01' in having a less upright and less branched plant habit, a less floriferous blooming habit, flowers and sepals that show color later in the season, and leaves that are lighter green in color and less ovate in form. 'Minabaut1' can be compared to *Abelia chinensis* cultivar 'Keiser' (U.S. Plant Pat. No. 21,632) that differs from 'Minabaut01' in having a less vigorous and upright habit, flowers that are longer and larger in size, and sepals are darker red in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include website listings by the Polish Nurserymen Association, Grasslands Nursery, Minier, and GradinaMax, Zahradnictvi Spomysl, and Promesse de fleurs.

BRIEF DESCRIPTION OF THE DRAWINGS

The accompanying color photographs illustrate the overall appearance and distinct characteristics of the new *Abelia*. The photographs were taken of a two-year-old plant as grown outdoors in a 4-liter container in La Menitre, France.

The photograph in FIG. 1 provides a view of a plant of 'Minabaut01' in bloom.

Figure 1:
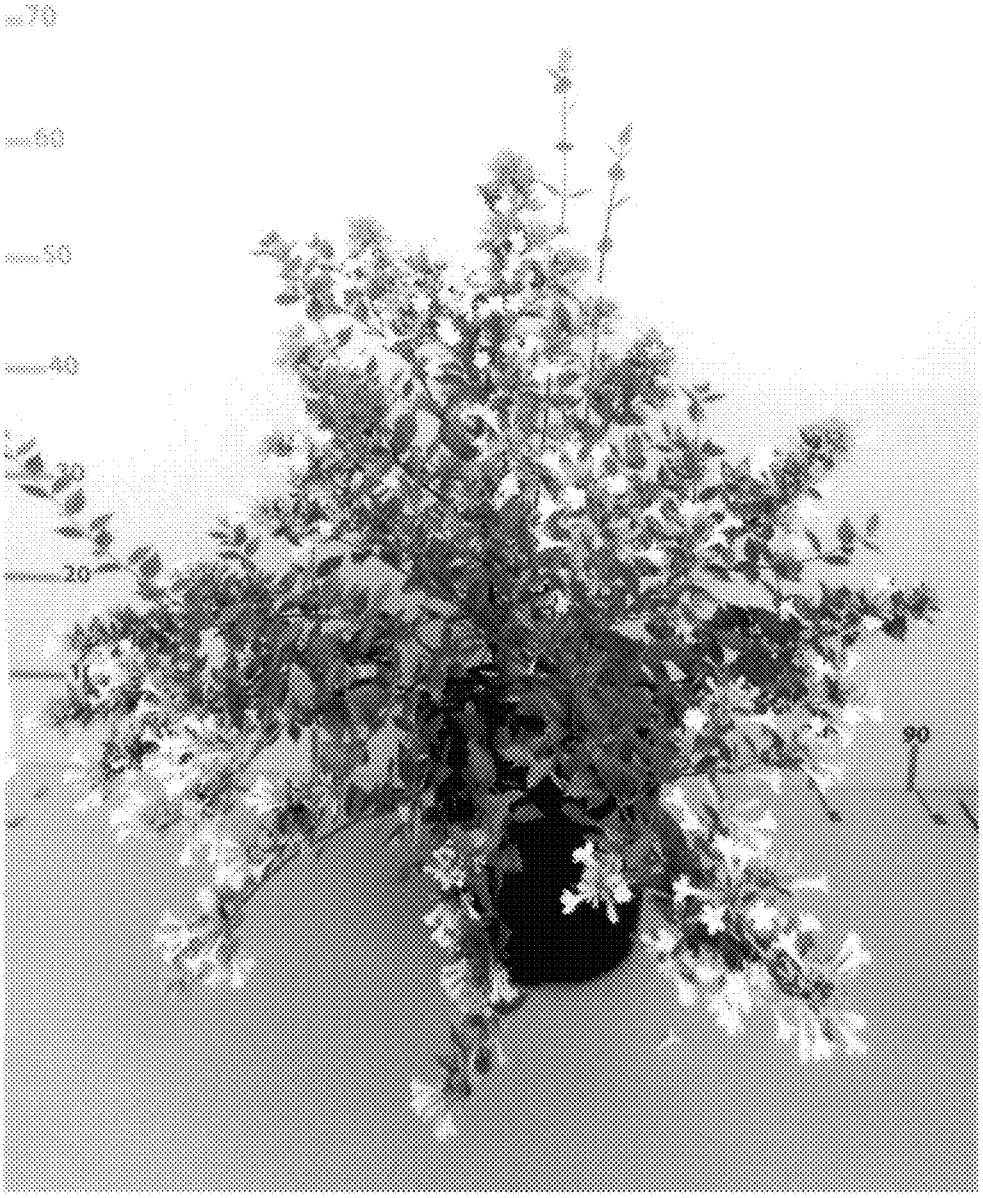
Figure 2:
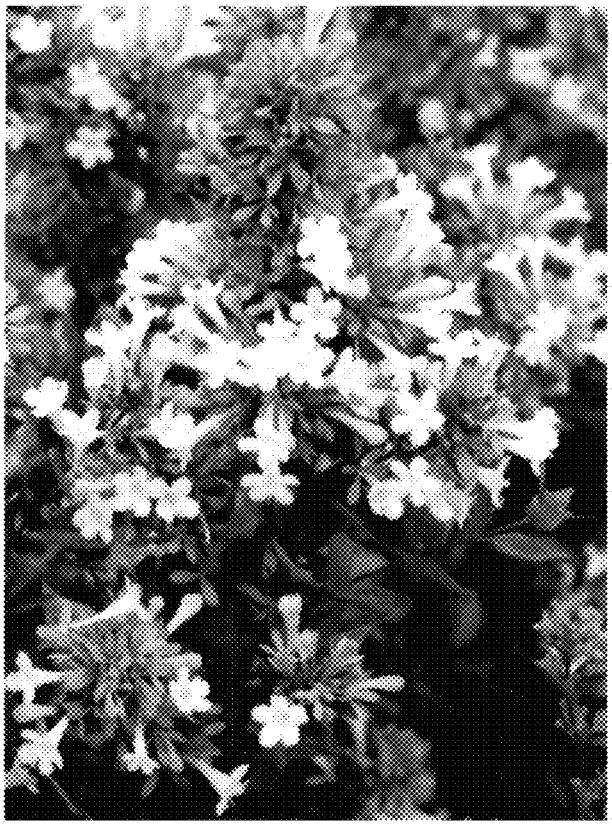

The photograph in FIG. 2 provides a close-up view of the inflorescences of 'Minabaut01'.

Figure 3:
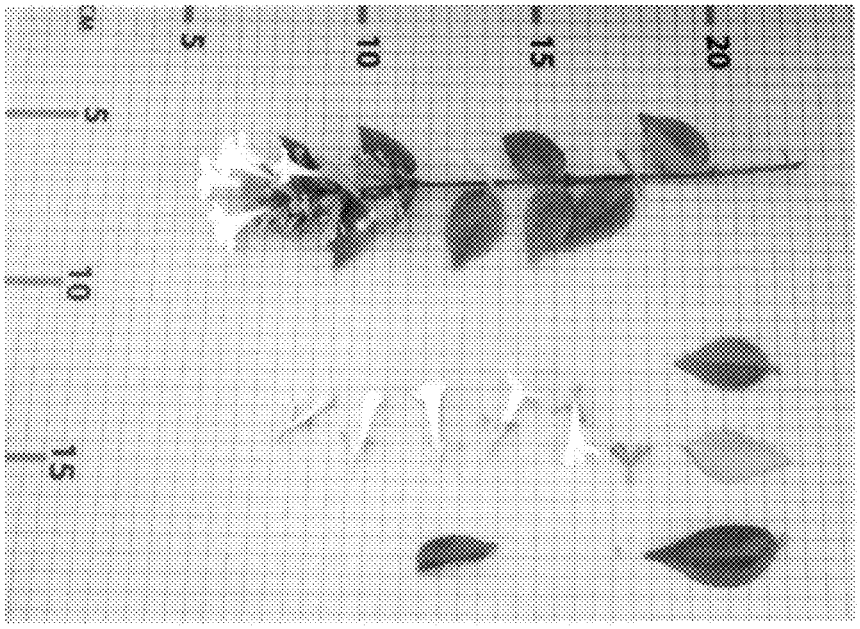

The photograph in FIG. 3 provides a view of a single inflorescence with dissected flowers and leaves.

The colors in the photographs are as close as possible with the photographic and printing technology utilized and the color values cited in the Detailed Botanical Description accurately describe the colors of the new *Abelia*.

DETAILED BOTANICAL DESCRIPTION

The following is a detailed description of 2.5 year old plant as grown outdoors in the ground in a trial field in Cottage Grove, MN. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—August to October in Newport, Minnesota.

*Plant type*.—Semi-evergreen flowering shrub.

*Plant habit*.—Upright spreading, well branched.

*Height and spread*.—An average of 80 cm in height and 117 cm in spread as a 2.5-year-old plant as grown in the landscape.

*Cold hardiness*.—At least in U.S.D.A. Zones 6 to 9.

*Diseases and pests*.—No susceptibility or resistance to diseases or pests has been observed.

*Root description*.—Fine and fibrous, prolific and well branched, 164D in color.

*Propagation*.—Stem cuttings.

*Root development*.—Roots initiate in an average of 6 weeks, a young plant is produced from a rooted cutting in 1 year.

*Growth rate*.—Vigorous.

Stem description:

*Stem color*.—Young; 45A, mature; N167A, older bark; 156B and 162B.

*Stem size*.—Main branch; 2 cm in diameter, lateral branches; 52 cm in length, 5 mm in diameter, tertiary branches; 8 cm in length, 1 mm in diameter.

*Stem quantity*.—10 main stems, 40 lateral branches per main stem.

*Stem arrangement*.—Opposite and whorled.

*Stem shape*.—Round.

*Stem surface*.—Young; glossy and moderately covered with fine, stiff, short pubescent hairs, NN155A in color, too small to measure size, slightly rough to the touch, mature; exfoliating, striate, matte, older bark; dry, glabrous and matte.

*Stem strength*.—Strong, flexible.

*Internode*.—An average of 1.5 cm in length.

*Branching habit*.—Freely branching, pruning enhances lateral branching.

Foliage description:

*Leaf division*.—Simple.

*Leaf attachment*.—Petiolate.

*Leaf arrangement*.—Opposite, whorled.

*Leaf number*.—An average of 22 per stem 15 cm in length.

*Leaf shape*.—Ovate.

*Leaf size*.—An average of 2 cm in length and 1 cm in width.

*Leaf apex*.—Acute.

*Leaf base*.—Cuneate.

*Leaf surface*.—Upper surface; glossy and sparsely covered with fine, stiff, short pubescent hairs, translucent, NN155A in color, too small to measure size, lower surface; glossy, glabrous, main vein sparsely covered with fine, stiff, short pubescent hairs, translucent, NN155A in color, too small to measure size.

*Leaf venation*.—Pinnate, color; both surfaces match leaf color.

*Leaf margin*.—Slightly dentate to entire.

*Leaf color*.—Young upper surface; 146A and 147A, heavily flushed with 200B, margins 200B, young lower surface; 146B, mature and fall upper surface; 147A, and mature and fall lower surface; 146A.

*Petioles*.—An average of 1 mm in diameter and 2 mm in length, both surfaces glossy, and glabrous, color; young upper and lower surface; 185A, mature upper and lower surface; 174A.

Flower description:

*Inflorescence type*.—Terminal and axillary panicles of campanulate flowers.

*Inflorescence aspect*.—Upwards and outwards.

*Inflorescence size*.—An average of 9 cm in height and 8 cm in width.

*Inflorescence density of flowers*.—Dense.

*Flower fragrance*.—Moderate, pleasant, rose-like fragrance.

*Flower quantity*.—An average of 30 flowers per inflorescence.

*Flower lastingness*.—An average of 7 days, self-cleaning, persistent showy sepals last for about 5 months.

*Flower buds*.—Obelliptic and phallic in shape, an average of 2 mm in diameter and 1 cm in length, 50 per inflorescence, surface; young buds glossy, mature buds glabrous, satiny and matte, color: young buds before sepals open; 146A, maturing buds; a blend of 182A and 162B, very top all 182A, base all 162B, mature buds before burst; top 186B, base and mid-section NN155D.

*Flower aspect*.—All directions.

*Flower shape*.—Campanulate with base fused.

*Flower size*.—2 cm in depth and 1.2 cm in diameter.

*Flower tube*.—1.5 cm in length, 4 cm in width at the widest point, inner surface is satiny and densely covered with tomentose hairs NN155D in color, up to 1 mm in length, color; inner and outer surface NN155D, outer surface very faintly flushed with 62C.

*Petals*.—An average of 5, spatulate in shape, an average of 3 mm in length and 4 mm in width, margins are slightly undulate, obtuse apex, 80% fused base, upper surface has a luster in the sun, satiny and densely covered with tomentose hairs NN155D in color, up to 1 mm in length, color; upper and lower surface when opening and fully open NN155D with specks of N74A.

*Sepals*.—5, an average of 2 mm in width and 6 mm in length, elliptical in shape, entire margin, bluntly acute apex, fused, cuneate base, smooth upper and lower surface, color; young upper and lower surfaces base 140B, mid-section to top 182A to 182B, mature upper and lower surfaces a blend of 159A and 173A, 159A more so at the base.

*Peduncles*.—An average of 5 mm in length and 2 mm in diameter, strong, 187A in color, surface is glossy and moderately covered with tomentose pubescence, translucent, closest to NN155D in color, too small to measure size.

*Pedicels*.—An average of 2 mm in length and 1 mm in diameter, moderately strong, 187A in color, surface is glossy and moderately covered with tomentose pubescence, translucent, closest to NN155D in color, too small to measure size.

Reproductive organs:

*Gynoecium*.—Pistil; 1, an average of 1.2 cm in length, glabrous surface, stigma; round in shape, flattened, an average of 1 mm in diameter, 150C in color, style; an average of 1.1 cm in length and 1 mm in width, 149D in color, ovary; inferior, an average of 5 mm in length and 0.5 mm in width, 142A in color.

*Androecium*.—Stamens; 4, 1.5 cm in length, anthers; an average of 2 mm in width and 1 mm in depth, dorsifixed, N79A in color, densely covered with pollen, filaments; an average of 1.4 cm in length and 0.5 mm in width, N155D in color, pollen is high in quantity, NN155D in color.

*Fruit and seed*.—None observed to date.

It is claimed:

1. A new and distinct cultivar of *Abelia* plant named 'Minabaut01' as herein illustrated and described.

* * * * *